United States Patent
Reddy et al.

(10) Patent No.: US 9,193,674 B2
(45) Date of Patent: Nov. 24, 2015

(54) PROCESS FOR THE PREPARATION OF AMINOACRYLIC ACID DERIVATIVES

(71) Applicant: Council of Scientific & Industrial Research, New Delhi (IN)

(72) Inventors: Dumbala Srinivasa Reddy, Maharashtra (IN); Kashinath Komirishetty, Maharashtra (IN); Siva Swaroop Pandrangi, Maharashtra (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days.

(21) Appl. No.: 14/350,872

(22) PCT Filed: Oct. 15, 2012

(86) PCT No.: PCT/IN2012/000683
§ 371 (c)(1),
(2) Date: Apr. 10, 2014

(87) PCT Pub. No.: WO2013/054366
PCT Pub. Date: Apr. 18, 2013

(65) Prior Publication Data
US 2014/0256976 A1  Sep. 11, 2014

(30) Foreign Application Priority Data
Oct. 14, 2011 (IN) .................... 2958/DEL/2011

(51) Int. Cl.
C07C 231/10 (2006.01)
C07D 309/06 (2006.01)
C07C 231/12 (2006.01)

(52) U.S. Cl.
CPC ............. C07C 231/10 (2013.01); C07C 231/12 (2013.01); C07D 309/06 (2013.01); *C07B 2200/07* (2013.01)

(58) Field of Classification Search
CPC ............................ C07C 235/12; C07C 235/26
See application file for complete search history.

(56) References Cited

PUBLICATIONS

Villa Mattew, Doctoral Dissertation, Jan. 2009 Department of Chemistry, University of Glasgow,UK.*

Sewell et al., "Fast and Flexible Synthesis of Pantothenic Acid and CJ-15, 801," Organic Letters 13(4):800-803, XP55052154 (2011).
Nicolaou et al., "Synthesis of Imides, N-Acyl Vinylogous Carbamates and Ureas, and Nitriles by Oxidation of Amides and Amines with Dess-Martin Periodinane," Angewandte Chemie International Edition, (44)37: 5992-5997, XP55052170 (2005).
Han et al., "Copper-Mediated Synthesis of N-Acyl Vinylogous Carbamic Acids and Derivatives: Synthesis of the Antibiotic CJ-15,801," Organic Letters, 6(1):27-30, XP55052152 (2004).
Kashinath et al., "A green synthetic route to antimalarial and antibacterial agent CJ-15,801 and its isomer cis-CJ-15,801," RSC Advances, 2(9):3596, XP55052155 (2012).
European Patent Office, International Search Report for PCT/IN2012/000683, dated Feb. 12, 2013.
International Preliminary Report of Patentability for International Patent Application No. PCT/IN2012/000683 dated Apr. 15, 2014.
Written Opinion of the International Searching Authority for International Patent Application No. PCT/IN2012/000683 dated Feb. 12, 2013.

* cited by examiner

*Primary Examiner* — Yong Chu
*Assistant Examiner* — Ana Z Muresan
(74) *Attorney, Agent, or Firm* — Fish & Richardson P.C.

(57) ABSTRACT

The present invention relates to a simple, economical and short synthesis for the class of compounds chemically belonging to amino acrylic acids of general formula I exhibiting both antibacterial and anti-plasmodium (anti-malarial) activity, in good yield and purity. Process for the preparation of said compound comprising heating amine (A) and pantolactone or substituted pantolactone (B) in a solvent selected from cyclohexane, benzene, toluene, xylene, diphenyl ether; anisole, dioxane, etc. at a temperature in the range of 110-150° C. for about 24 hrs followed by further raising the temperature of the mixture to a temperature in the range of 200-230° C. for period in the range of 15 to 25 min followed by cooling the crude reaction mixture to room temperature to obtain compound of general Formula I.

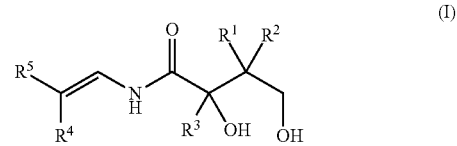

(I)

7 Claims, 6 Drawing Sheets

PROCESS FOR THE PREPARATION OF AMINOACRYLIC ACID DERIVATIVES

TECHNICAL FIELD OF THE INVENTION

The present invention relates to a simple, economical and short synthesis for the class of compounds chemically belonging to amino acrylic acids of general formula I exhibiting both antibacterial and anti-plasmodium (anti-malarial) activity, in good yield and purity.

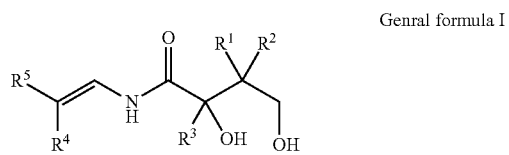

Genral formula I

BACKGROUND AND PRIOR ART OF THE INVENTION

The treatment of infections due to *Staphylococcus aureus* was revolutionized in the 1940s by the introduction of the antibiotic penicillin. However, most strains of *Staphylococcus aureus* are now resistant to penicillin. In the early 1960s, a new type of penicillin antibiotic called methicillin was developed which was used to treat infections due to β-lactamase-producing strains of *Staphylococcus aureus*.

'MRSA' which stands for methicillin-resistant *Staphylococcus aureus*, is a type of *Staphylococcus aureus* that is resistant to the antibacterial activity of methicillin and other related antibiotics of the penicillin class. In addition to MRSA, emergence of almost untreatable vancomycin-resistant enterococci and the threat of transfer of glycopeptide resistance to *Staphylococcus aureus* have led to a new and unexpected public health problem in hospitals and the community.

Further, each year the human malaria parasite, *Plasmodium falciparum*, infects hundreds of millions of people and kills more than one million children under the age of five. Although progress towards a vaccine is being made, the lack of a commercially available vaccine and the increasing prevalence of resistance to most of the currently available antimalarials have intensified the need for new antimalarials and the identification of novel drug targets.

The intra-erythrocytic stage of *P. falciparum* (the stage of the parasite's lifecycle responsible for the morbidity and mortality associated with malaria) is observed to be reliant on the uptake of the water soluble vitamin pantothenic acid (Vitamin B5) which is phosphorylated by pantothenate kinase to coenzyme A. Many pantothenic acid analogues have been tested for their ability to inhibit parasite growth in vitro, and in a number of animal models of malaria; however, these have had limited success.

Accordingly, the discovery and development of new anti-multi-drug resistant bacterial agents therefore remains the need of the hour. Recently, novel N-acyl vinylogous carbamic (β-amido acrylic) acid containing molecule, CJ-15,801 was reported as an inhibitor of multiple-drug-resistant (MDR) *Staphylococcus aureus* strains.

In 2001, Sugie's group from Pfizer isolated the antibiotic CJ-15,801 from the fermentation broth of a fungus, *Seimatosporium* sp. CL28611.

References may be made to an article titled "CJ-15,801, a fungal natural product, inhibits the intra erythrocytic stage of *Plasmodium falciparum* in vitro via an effect on pantothenic acid utilization" by Kevin J. Saliba et.al in Molecular & Biochemical Parasitology 141 (2005) 129-131, discloses antiplasmodial activity of CJ-15,801 against *P. falciparum*. It is reported in the said article that CJ-15,801 differs from pantothenic acid only in that it has a double bond in place of a single bond between carbons 2 and 3 as shown in figure below, and the compound CJ-15,801 exerts its effect on the parasite by inhibiting the utilization of pantothenic acid by the parasite:

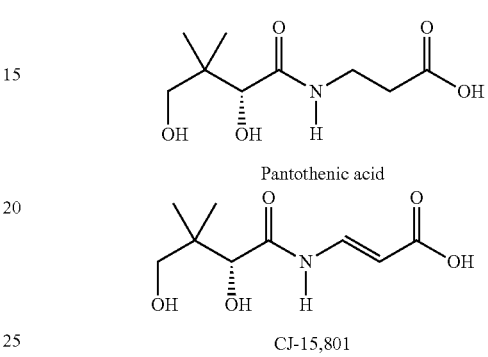

Pantothenic acid

CJ-15,801

References may be made to an article titled "Copper-Mediated Synthesis of N-Acyl Vinylogous Carbamic Acids and Derivatives: Synthesis of the Antibiotic CJ-15,801" by Chong Han reports copper(I)-mediated coupling of amides with β-iodo-acrylates and acrylamides to prepare N-acyl vinylogous carbamates and ureas. The N-acyl vinylogous carbamic acid antibiotic CJ-15,801 and analogues is also prepared using this methodology (FIG. 1).

References may be made to an article titled "Synthesis of Imides, N-Acyl Vinylogous Carbamates and Ureas, and Nitriles by Oxidation of Amides and Amines with Dess-Martin" published in Angew. Chem. Int. Ed. 2005, 44, 5992-5997, by K. C. Nicolaou et.al discloses total synthesis of the cis isomer of antibiotic CJ-15,801 as given in FIG. 3. Accordingly, the process includes allylation of β-alanine followed by subsequent reaction of the resulting amino ester with D-(−)-pantolactone in refluxing toluene to obtain dial. This is followed by acetonide formation within diol to obtain a compound whose oxidation with DMP gave a mixture of the N-acyl vinylogous carbamates in cis and trans form in approximately 8:1 ratio, in favor of the cis isomer. The cis compound was converted into cis-CJ-15,801 by sequential cleavage of the acetonide (BiCl$_3$) and allyl ester ([Pd(PPh3)$_4$]) protecting groups (FIG. 2).

The prior art processes as described above for the synthesis of N-acyl vinylogous carbamic acids and derivatives including CJ-15,801 suffer from several drawbacks including being very long and strenuous routes for synthesis of the compound and involves the use of costly reagents which makes the process uneconomical. Further, the routes of synthesis of N-acyl vinylogous carbamic acids and derivatives thereof including CJ-15,801 in the prior art do not lead to pure isomers, adding a cumbersome step to the synthesis of separation or resolution of isomers.

To fulfill this need in the art, the present inventors disclose herein a simple and economical route for synthesis of a class of compounds belonging to amino acrylic acid including CJ-15,801 having both antibacterial and anti-plasmodium activity. It is also the object of the current invention to provide the process for the preparation of compounds which directly lead to the formation of pure-isomer of the desired compound.

OBJECTS OF THE INVENTION

Main objective of the present invention is to provide a simple, economical and short synthesis for the class of compounds chemically belonging to amino acrylic acids of general formula I.

Another objective of the present invention is to provide a process for the preparation of compounds of formula I exhibiting both antibacterial and anti-plasmodium (anti-malarial) activity, in good yield and purity.

DETAILED DESCRIPTION OF THE INVENTION

The present invention discloses a simple, economical and short process for the preparation of a class of compounds of general formula I belonging to amino acrylic acids, its esters, stereoisomers and pharmaceutically acceptable salts thereof exhibiting both antibacterial and anti-plasmodium activity, in good yield and purity.

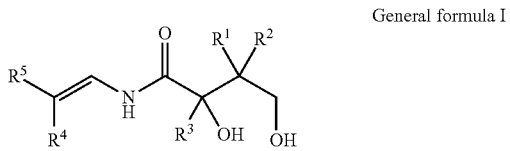

General formula I

In general formula I, $R^1$, $R^2$, and $R^3$ are independently selected from the group consisting of hydrogen; —$C_1$-$C_{15}$ alkyl; $C_1$-$C_{15}$ alkenyl; —$C_1$-$C_{15}$ alkynyl; phenyl; aralkyl; conjugated aromatic group; which may optionally be substituted with halo; nitro; alkoxy; cyano; hydroxy; amido, or amino groups; or $R^1$ and $R^2$ may be taken together to form a cyclic compound which may optionally contain 1 to 4 heteroatoms, optionally the cyclic compound may contain a carbonyl group; or $R^1$ and $R^2$ are independently selected from halo group, nitro group, alkoxy group, cyano group, hydroxyl group; or amido or amino groups;

In general formula I, $R^4$ and $R^5$ are independently selected from hydrogen; —$C_1$-$C_{15}$ alkyl; —$C_1$-$C_{15}$ alkenyl; —$C_1$-$C_{15}$ alkynyl; phenyl; aralkyl; conjugated aromatic group; which may optionally be substituted with halo; nitro; alkoxy; cyano; hydroxy; amido or amino groups; or $R^4$ and $R^5$ independently are COOR; or $R^4$ and $R^5$ may be taken together to form a cyclic compound which may optionally contain 1 to 4 heteroatoms; optionally the cyclic compound may contain a carbonyl group; and R is independently selected from hydrogen, —$C_1$-$C_{15}$ alkyl, —$C_1$-$C_{15}$ alkenyl; —$C_1$-$C_{15}$ alkynyl; phenyl; aralkyl; which may optionally be substituted with the substituents selected from halo; nitro; alkoxy; cyano; hydroxy; amido or amino groups.

The pharmaceutically acceptable salt includes both acid and base additidn salts. The acid addition salts are formed with both inorganic acids such as hydrochloric acid, hydrobromic acid, phosphoric acid, sulfuric acid, nitric acid and the like; the organic acids are selected from but not limited to acetic acid, benzenesulfonic acid, benzoic acid, cinnamic acid, citric acid, formic acid, fumaric acid, and the like. The base addition salts are derived from inorganic bases which include, but are not limited to, sodium, potassium, lithium, ammonium, calcium, magnesium, iron, zinc, copper, manganese, aluminum salts and the like; from organic bases such as salts of ammonia, primary, secondary, and tertiary amines, cyclic amines etc.

Figure 1:
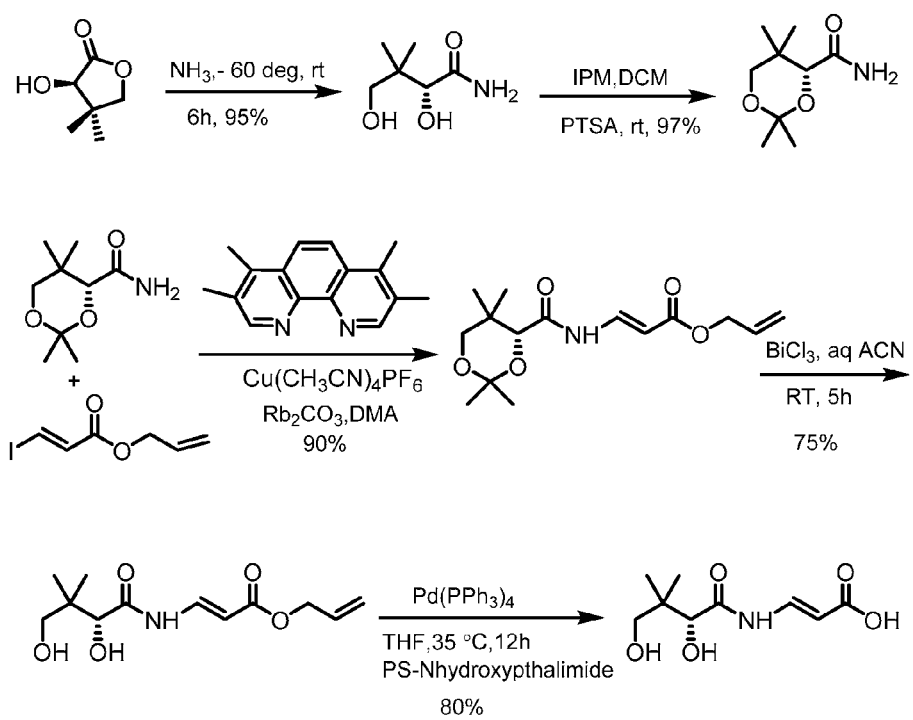
FIG. 1 represents steps for the preparation of N-acyl vinylogous carbamic acid antibiotic CJ-15,801 and analogues by Chong Han.
Figure 2:
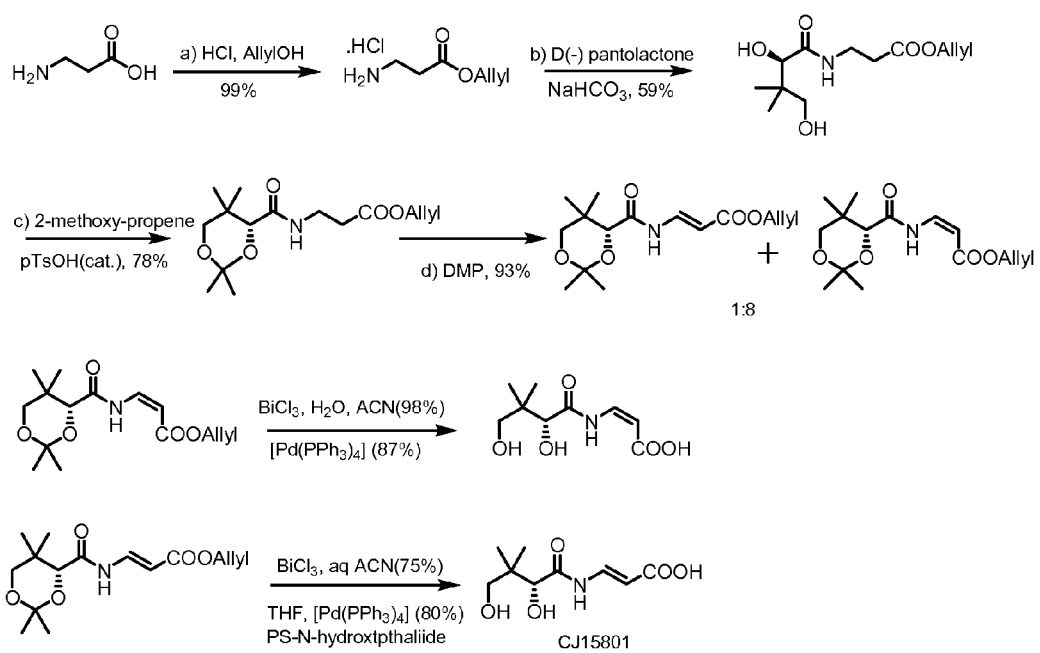
FIG. 2 represents steps for the preparation of cis-CJ-15,801 by sequential cleavage of the acetonide (BiCl3) and allyl ester ([Pd(PPh3)4]) protecting groups reported by K. C. Nicolaou.
Figure 3:
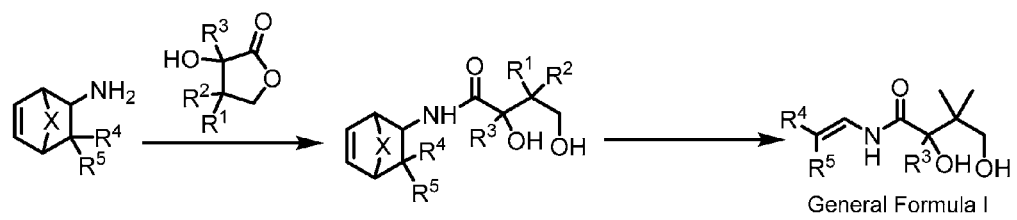
FIG. 3 represents steps for the preparation of compounds of general formula I.

Present invention provides a synthesis for the preparation of class of compounds belonging to amino acrylic acids of the general formula I including heating amine (A) and pantolactone or substituted pantolactone (B) in a solvent selected from cyclohexane, benzene, toluene, xylene, diphenylether, lanisole, dioxane, etc. at a temperature in the range of 110-150° C. for about 24 hrs followed by further raising the temperature of the mixture to a temperature in the range of 200-230° C. for a period in the range of 15 to 25 min, cooling the crude reaction mixture to room temperature (25 to 30° C.) to obtain compounds of general Formula I (FIG. 3). The purification and isolation of the cis or trans isomer obtained by the above process may optionally be carried out by silica gel column chromatography.

The process encompasses stereoisomer due to presence of chiral group along with E or Z geometric isomers. The amine and the pantolactone (D or L) used as substrates in the process are represented by formula (A) and formula (B)

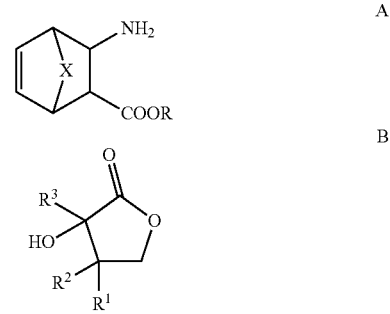

A

B wherein X is independently selected from the group consisting of $CH_2$, O, NR', alkylidine or cyclopropyl;

R is independently selected from hydrogen, —$C_1$-$C_{15}$ alkyl, —$C_1$-$C_{15}$ alkenyl; —$C_1$-$C_{15}$ alkynyl; phenyl; aralkyl; which may optionally be substituted with halo; nitro; alkoxy; cyano; hydroxy; amido, or amino group;

$R^1$, $R^2$, $R^3$ are independently selected from hydrogen; —$C_1$-$C_{15}$ alkyl; $C_1$-$C_{15}$alkenyl; —$C_1$-$C_{15}$ alkynyl; phenyl; aralkyl; conjugated aromatic group; which may optionally be substituted with halo; nitro; alkoxy; cyano; hydroxy; amido, or amino groups; or $R^1$ and $R^2$ may be taken together to form a cyclic compound which may optionally contain 1 to 4 heteroatoms, optionally the cyclic compound may contain a carbonyl compound; or $R^1$, $R^2$, are independently selected from halo; nitro; alkoxy; cyano; hydroxyl; amido or amino groups.

Figure 4:
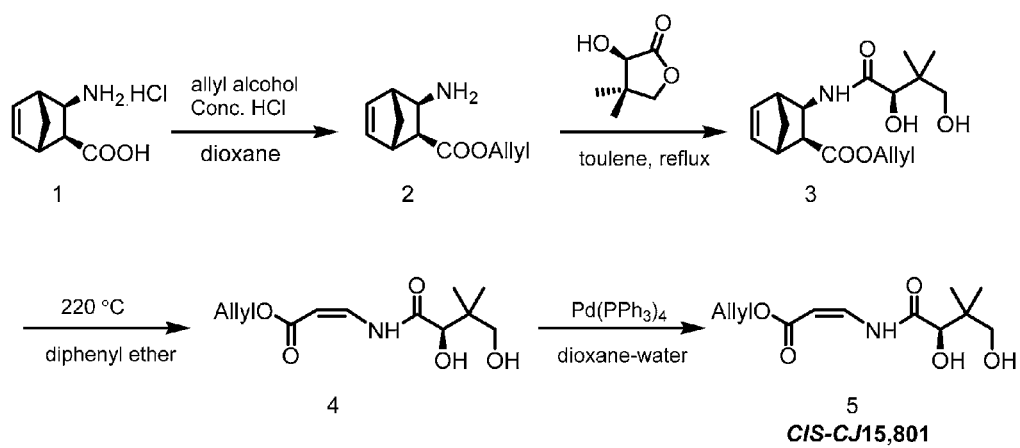
FIG. 4 represents steps for the preparation of the compound of formula 5 cis-CJ15801.

The process for the preparation of CJ-15,081 (5) includes heating a mixture of amine (2) and D-(−)-pantolactone in a solvent at a temperature in the range of 110-150° C. for about 24 hrs followed by raising the temperature of the mixture to a temperature in the range of 200-230° C. for 15-25 min, cooling the crude reaction mixture to 25 to 30° C. and further purifying by silica gel column chromatography to yield cis isomer (4) (FIG. 4).

Deallylation of compound of formula (4) is carried in presence of palladium catalyst such as $PdCl_2$, $PdCl_2(PPh_3)$, $Pd(PPh_3)_4$ preferably $Pd(PPh_3)_4$ in a solvent selected from water alone or in combination with water miscible solvents, ethers such as THF, dioxane, ketones such as acetone to obtain cis CJ-15,801(5).

The amine (2) is obtained by refluxing a mixture of hydrochloride salt of amino acid of formula (1) and allyl alcohol in a solvent selected from aliphatic or aromatic hydrocarbon, ethers such as THF, dioxane, dimethyl ether, ketones etc. and conc. HCl for about 4-5 hrs. The formation of amine (2) from (1) and its further, conversion to cis CJ-15,801 is given in FIG. 5. The hydrochloride salt of amino acid (1) is prepared according to the procedure described in the art [Forro, E.; Fulop, F. Tetrahedron Asymmetry 2004, 15, 573].

Present invention discloses the preparation of (R,E)-(2,4-dihydroxy-3,3-dimethylbutanamido) acrylic acid (6) by a process as described herein above.

The compounds of the present invention possess antibacterial activity against a wide spectrum of Gram-positive and Gram-negative bacteria, aerobic and anaerobic organisms such as *Staphylococcus, Lactobacillus, Streptococcus, Escherichia, Enterobacter, Pseudomonas, Proteus, Citrobacter, Baccillus, Clostridium, Salmonella*, and other organisms. Also, the compounds of the present invention possess antibacterial activity against bacterial species resistant to conventional [beta]-lactams, such as MRSA. Further, the compounds of the instant invention are effective as antiplasmodium agent for the treatment of malaria. The compound of formula (I) disclosed herein is present in the composition in an amount which is effective to treat the disease or the condition caused by the bacterial strains mentioned above.

Present invention provides a pharmaceutical composition comprising a compound of general formula I or a stereoisomer, or ester or pharmaceutically acceptable salt thereof, and a pharmaceutically acceptable carrier, diluent or excipient.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres.

Present invention relates to administering 'an effective amount' of the 'composition of invention' to the subject suffering from said disease. Accordingly, compound of formula I and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

Pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

EXAMPLES

Following examples are given by way of illustration therefore should not be construed to limit the scope of the invention.

Example 1

(1S*,2S*,3R*,4R*)-Allyl 3-aminobicyclo[2.2.1]hept-5-ene-2-carboxylate (2)

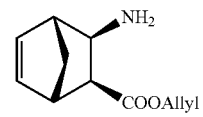

To a mixture containing 1 (1.0 g, 5.2 mmol) and allyl alcohol (3.6 mL, 52 mmol) in dioxane (20 mL) was added 10N HCl (cat) (0.5 mL) and heated to reflux. After 4h, the dioxane was removed under vacuum from the reaction mixture and adjusted to pH 8 with saturated aq. $NaHCO_3$. The aqueous layer was extracted with ethyl acetate (2×100 mL) and the combined organic layers were washed with water (1×50 mL), brine (1×25 mL), dried ($Na_2SO_4$) and concentrated under reduced pressure to afford crude 2 as brown thick mass (800 mg, 80%), which was forwarded to next reaction without any further purification.

IR $\nu_{max}$ (film): 3383, 3063, 2979, 2882, 1728, 1647 $cm^{-1}$; $^1H$ NMR (500 MHz, $CDCl_3$) δ:6.11 (2H, m), 5.90 (1H, ddt, J=17.0, 10.3, 5.8 Hz), 5.30 (1H, dd, J=17.0, 1.5 Hz), 5.20 (1H, dd, J=10.3, 1.2 Hz), 4.57 (2H, m), 3.21 (1H, dd, J=7.9, 1.2 Hz), 2.93 (1H, m), 2.53 (1H, m), 2.45 (1H, dd, J=7.9, 1.8 Hz), 2.04 (1H, m), 1.51 (1H, m), 1.46 (2H, br s); $^{13}C$ NMR (125 MHz, $CDCl_3$) δ:173.7, 138.0, 137.2, 132.2, 118.3, 65.0, 54.6, 50.1, 48.9, 44.6, 43.9; LCMS [M+H]$^+$: 194; HRMS calculated for $C_{11}H_{15}NNaO_2^+$ [M+Na]$^+$: 216.1000, found 216.1003.

Example 2

(1S,2S,3R,4R)-Allyl3-((R)-2,4-dihydroxy-3,3-dimethylbutanamido)bicyclo[2.2.1]hept-5-ene-2-carboxylate and (1R,2R,3S,4S)-Allyl3-((R)-2,4-dihydroxy-3,3-dimethylbutanamido)bicyclo[2.2.1]hept-5-ene-2-carboxylate (3) (FIG. 4)

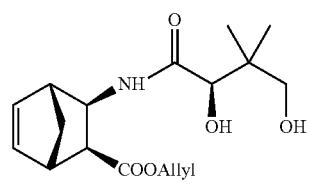

A mixture of 2 (200 mg, 1 mmol), and D-(−)-pantolactone (270 mg, 2 mmol) in toluene (10 mL) were heated to reflux for 24 h and the reaction progress was monitored through TLC.

After considerable amount of compound 2 was consumed with no further progress in the reaction, toluene was removed under vacuum. The crude mixture was diluted with ethyl acetate (20 mL) and the organic layer was washed with 1N HCl (1×5 mL), water (1×10 mL), brine (1×5 mL), dried over $Na_2SO_4$ and concentrated under vacuum. The crude residue was purified by silica gel column chromatography by eluting with methanol:DCM (2:98) to afford a yellow gummy mass of 3 (198 mg, 60%) as inseparable diastereomeric mixture. The diastereomeric ratio of 3 (~3:2) was determined by $^1$H NMR and HPLC analysis.

(IR $v_{max}$ (film): 3386, 2977; 2877, 1721, 1648, 1521 cm$^{-1}$; $^1$H NMR (500 MHz, CDCl$_3$): (mixture) δ 7.67 (1H, m), 6.20 (1H, m), 6.18 (1H, m), 5.86 (1H, ddt, J=17.0, 10.3, 5.8 Hz), 5.26 (1H, m), 5.20 (1H, m), 4.53 (2H, m), 4.13 (1H, m), 3.94 (1H, d, J=7.3 Hz), 3.43 (2H, m), 2.96 (1H, m), 2.69 (1H, m), 2.62 (1H, m), 1.97 (1H, m), 1.54 (1H, m), 0.94 (3H, d, J=14.0 Hz), 0.86 (3H, d, J=18.3 Hz); $^{13}$C NMR (125 MHz, CDCl$_3$): (mixture) δ 173.9 (2C overlapped), 172.8, 172.7, 138.3 (2C overlapped), 137.1, 137.0, 131.7, 131.6, 118.7, 118.6, 77.6, 77.3, 71.2, 70.9, 65.6, 65.5, 50.7 (2C), 48.5 (2C overlapped), 46.4, 46.3, 45.9, 45.8, 44.3 (2C overlapped), 39.2, 39.1, 21.0, 20.9, 20.2 (2C); LCMS [M+Na]$^+$: 346; HRMS calculated for $C_{17}H_{25}NNaO_5^+$ [M+Na]$^+$: 346.1630, found 346.1613.

Example 3

Synthesis of cis CJ15,801: (R,Z)-(2,4-dihydroxy-3,3-dimethylbutanamido)acrylic acid (5)

Procedure I: (R,Z)-allyl 3-(2,4-dihydroxy-3,3-dimethylbutanamido)acrylate (4) (FIG. 4)

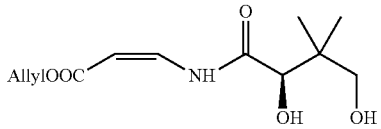

4

A diastereomeric mixture of 3 (50 mg, 0.2 mmol) in diphenyl ether (5 mL) was heated to ~230° C. by inserting the reaction mixture in a pre-heated oil bath for 20 min.[2] The crude reaction mixture was cooled to room temperature i.e. 25° C. and purified through silica gel column chromatography by eluting with methanol:DCM (3:97) to afford (30 mg, 77%) of 4 as a brown colored mass. IR $v_{max}$ (film): 3408, 2962, 1695, 1634 cm$^{-1}$; $^1$H NMR (500 MHz, CDCl$_3$): δ 11.25 (1H, br d, J=11.6 Hz), 7.46 (1H, dd, J=11.6, 8.8 Hz), 5.93 (1H, ddt, J=17.2, 10.4, 5.6 Hz), 5.32 (1H, ddd, J=17.2, 2.9, 1.3 Hz), 5.24 (1H, overlapped dd, J=10.4, 1.3 Hz), 5.22 (1H, d, J=8.8 Hz), 4.63 (2H, m), 4.20 (1H, s), 3.58 (1H, d, J=10.8 Hz), 3.53 (1H, d, J=10.8 Hz), 1.03 (3H, s), 0.98 (3H, s); $^{13}$C NMR (125 MHz, CDCl$_3$): δ 171.8, 168.2, 136.9, 131.9, 118.4, 97.5, 78.1, 71.4, 64.8, 39.3, 20.9, 20.2; LCMS [M+Na]$^+$: 280. [α]$_D^{23}$=+26.2 (c=0.8, CHCl$_3$). Spectral data compared with that of reported data and was found to be identical.

Procedure II (One pot synthesis): (R,Z)-allyl 3-(2,4-dihydroxy-3,3-dimethylbutanamido)acrylate (4) (FIG. 4)

A mixture of amine 2 (250 mg, 1.3 mmol) and D-(−)-pantolactone (340 mg, 2.6 mmol) in diphenyl ether (15 mL) were heated to 130° C. for 24 h and the progress of the reaction was monitored through TLC. After considerable amount of pantolactone was consumed with no further improvement in the reaction, the temperature of the reaction mixture was further raised to 220° C. for 20 min. After the completion of reaction (TLC monitoring), the crude reaction mixture was cooled to room temperature 27° C. and purified by silica gel column chromatography eluting with methanol:DCM (3:97) to yield 202 mg (61%) of 4 as a brown colored mass.

Deallylation of compound of formula (4) was carried out by heating compound (4) in the presence of a palladium catalyst such as Pd(PPh$_3$)$_4$ in a dioxane-water mixture as per the procedure described in the art [Nicolaou, K. C.; Mathison, C. J. N. Angew. Chem., Int. Ed. 2005, 44, 5992] to obtain compound 5.

Example 4

Figure 5:
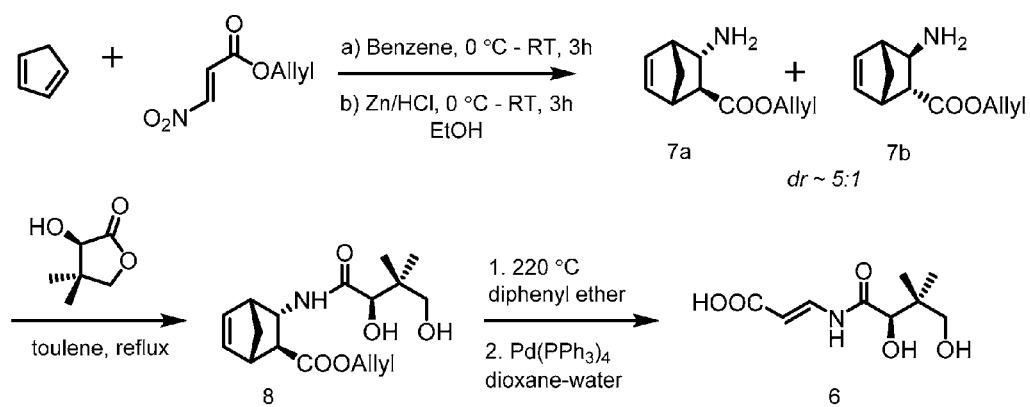
FIG. 5 represents steps for the preparation of the compound of formula 6 (015801).

(1S*,2S*,3S*,4R*)-Allyl 3-aminobicyclo[2.2.1]hept-5-ene-2-carboxylate and (1S*,2R*,3R*,4R*)-Allyl 3-aminobicyclo[2.2.1]hept-5-ene-2-carboxylate (7a and 7b) (FIG. 5)

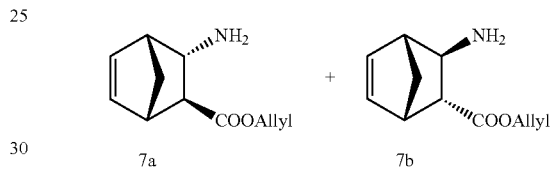

7a     7b

To a solution of β-nitro allyl acrylate (4.0 g, 25 mmol) in dry benzene (40 mL) at 0° C., was added slowly cyclopentadiene (2.1 mL, 25 mmol) (freshly prepared by cracking dicyclopentadiene dimer) and the resulting mixture was allowed to stir at room temperature i.e. 25° C. for 3h. The benzene was removed under vacuum to afford the crude diastereomeric mixture (~5.6 g) which was carried forward for the next step. $^1$H NMR analysis of a diastereomeric mixture revealed ~5:1 ratio of the endo and exo nitro cyclo adducts.

IR $v_{max}$ (film): 3419, 2954, 1732, 1621, cm$^{-1}$; $^1$H NMR (500 MHz, CDCl$_3$): (major) δ 6.48 (1H, dd, J=5.6, 3.2 Hz), 6.08 (1H, dd, J=5.6, 2.7 Hz), 5.93 (1H, ddt, J=17.0, 10.3, 5.8 Hz), 5.41 (1H, m), 5.34 (1H, dd, J=17.0, 1.5 Hz), 5.28 (1H, dd, J=10.3, 1.2 Hz), 4.65 (2H, d, J=5.8 Hz), 3.61 (1H, m), 3.25 (1H, m), 3.07 (1H, m), 1.69 (1H, app d, J=9.4 Hz), 1.62 (1H, ddd, J=9.4, 3.9, 1.8 Hz); $^{13}$C NMR (125 MHz, CDCl$_3$): (major) δ 171.8, 139.2, 133.6, 131.5, 118.9, 87.6, 66.1, 48.9, 47.7, 47.3, 46.2; HRMS calculated for $C_{11}H_{14}NO_4^+$ [M+H]$^+$: 224.0923, found 224.0924.

The above diastereomeric mixture (~5.6 g, 25 mmol) was placed in 250 mL round bottom flask together with ethanol (100 mL) and the resulting solution was charged with 10N HCl (30 mL) and zinc (13.0 g, 200 mmol) which was added portion wise, slowly to the reaction mixture and was allowed to stir for 3h. The reaction mixture was filtered through a short pad of celite bed and was washed with ethanol. The filtrate was concentrated under vacuum, diluted with water (50 mL), basified with NaHCO$_3$ to pH 8 and extracted with ethyl acetate (2×100 mL). The combined organic layers were washed with water (2×50 mL), brine (1×10 mL) and dried over Na$_2$SO$_4$ and concentrated under vacuum to afford 7a and 7b (~5:1) (3.9 g, 80%) as pale brown gummy mass.

IR $v_{max}$ (film): 3438, 2974, 2878, 1729, 1646 cm$^{-1}$; $^1$H NMR (500 MHz, CDCl$_3$): (major) δ 6.39 (1H, dd, J=5.4, 3.0 Hz), 6.20 (1H, dd, J=5.4, 2.7 Hz), 5.93 (1H, ddt, J=17.0, 10.3, 5.8 Hz), 5.30 (1H, dd, J=17.0, 1.5 Hz), 5.22 (1H, dd, J=10.3, 1.2 Hz), 4.58 (2H, app d, J=5.8 Hz), 3.69 (1H, app t, J=3.6 Hz), 2.98 (1H, m), 2.83 (1H, m), 1.77 (1H, dd, J=3.6, 2.4 Hz), 1.70 (1H, app d, J=8.8 Hz), 1.48 (1H, dd, J=8.8, 1.9 Hz), 1.41 (2H, br s). $^{13}$C NMR (125 MHz, CDCl$_3$): (major) δ 174.7, 138.8, 134.1, 132.2, 118.1, 65.2, 57.6, 55.1, 48.4, 47.3, 47.0; LCMS [M+H]$^+$: 194; HRMS calculated for $C_{11}H_{15}NNaO_2^+$ [M+Na]$^+$: 216.1000, found 216.0986.

Example 5

(1S,2S,3S,4R)-Allyl3-((R)-2,4-dihydroxy-3,3-dimethylbutanamido)bicyclo[2.2.1]hept-5-ene-2-carboxylate and (1R,2R,3R,4S)-Allyl3-((R)-2,4-dihydroxy-3,3-dimethylbutanamido)bicyclo[2.2.1]hept-5-ene-2-carboxylate (8) (FIG. 5)

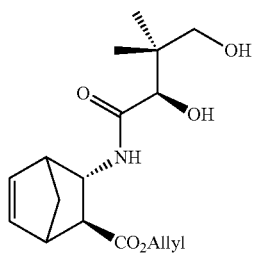

8

Prepared from the mixture 7a and 7b (0.5 g, 2.6 mmol) and D-(−) pantolactone (0.67 g, 5.2 mmol) in 61% yield as a mixture of four diastereomers by following the procedure for the synthesis of 3. The endo (8):exo (8) diastereomeric ratio (96:4) was determined by HPLC analysis (Chiralcel-OJ-H column, 220 nm, 95:5 Petroleum ether/i-PrOH, 1.0 mL/min, τ exo 7.4, 8.8 and endo 9.6, 11.3).

IR $v_{max}$ (film): 3407, 2960, 2876, 1732, 1651 cm$^{-1}$; $^1$H NMR (500 MHz, CDCl$_3$): (major) δ 6.65 (1H, m), 6.41 (1H, m), 5.88 (1H, m), 5.28 (1H, m), 5.20 (1H, m), 4.68 (1H, m), 4.58 (2H, m), 3.92 (1H, d, J=1.5 Hz), 3.42 (2H, d,J=8.5 Hz), 3.03 (2H, m), 1.94 (1H, ddd, J=21.3, 3.9, 2.1 Hz), 1.78 (1H, m), 1.50 (1H, m), 0.92 (3H, d, J=10.0 Hz), 0.83 (3H, d, J=13.4 Hz); $^{13}$C MAR (125 MHz, CDCl$_3$): (major) δ 173.7, 173.5, 173.1, 173.0, 139.6, 139.4, 134.1, 133.9, 131.9 (2C overlapped), 118.3, 118.2, 77.0 (2C overlapped), 71.0 (2C overlapped), 65.5, 65.4, 53.7, 53.4, 52.4, 52.6, 47.3, 47.0, 46.3, 46.2, 46.1, 45.8, 39.2 (2C overlapped), 21.1, 21.0, 20.0 (2C); LCMS [M+Na]$^+$: 346; HRMS calculated for $C_{17}H_{25}NNaO_5^+$ [M+Na]$^+$: 346.1630 found 346.1618 (3.46 ppm).

Example 6

Preparation of CJ-15,801(6) (FIG. 5)

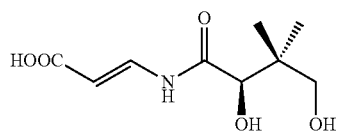

6

To the crude mixture containing 8 and 10 (8:2) (20 mg) in dioxane/water (4:1) was added Pd(PPh$_3$)$_4$ (0.2 eq) and stirred for 14 hrs. After the completion of reaction (TLC monitoring), the reaction mixture was dried (Na$_2$SO$_4$) and purified through preparative TLC by eluting with methanol:DCM (1:9) afforded ~1 mg of 6 as a brown colored mass.

$^1$H NMR (200 MHz, CD$_3$OD): δ 7.78 (1H, d, J=14.1 Hz), 5.71 (1H, d, J=14.1 Hz), 3.98 (1H, s), 3.49 (1H, d, J=10.8 Hz), 3.42 (1H, d, J=10.8 Hz), 0.94 (3H, s), 0.93 (3H, s). The $^1$H NMR data was compared with the reported data$^5$ and found to be identical.

Example 7

Figure 6:
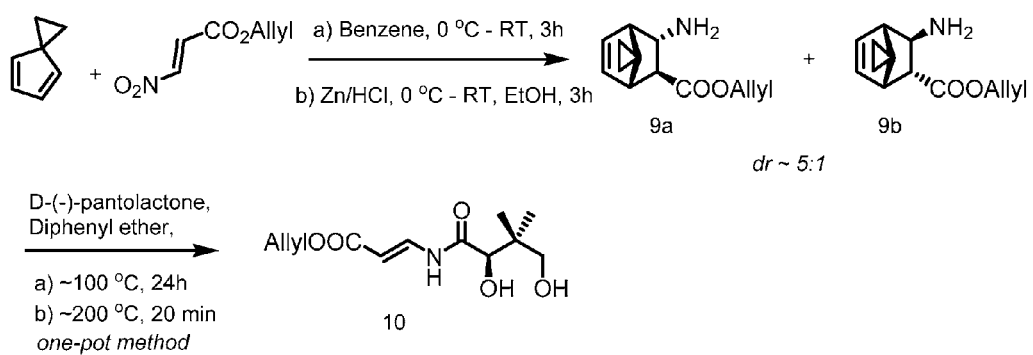
FIG. 6 represents steps for the preparation of the compound of formula 10.

(1S*,4S*,5S*,6S*)-Allyl5-aminospiro[bicyclo[2.2.1]hept[2]ene-7,1'-cyclopropane]-6-carboxylate (9a) and (1S*,4S*,5R*,6R*)-Allyl5-aminospiro[bicyclo[2.2.1]hept[2]ene-7,1'-cyclopropane]-6-carboxylate (9b) (FIG. 6)

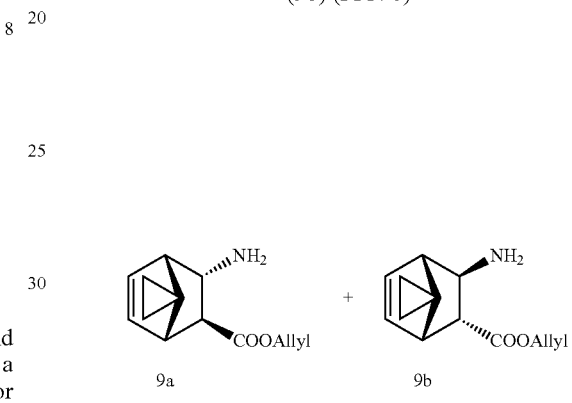

The nitro adduct was prepared from allyl β-nitro acrylate (1.0 g, 6.3 mmol) and spiro[2.4]hepta-4,6-diene$^6$ (0.6 mL, 6.3 mmol) as inseparable diastereomeric mixture (5:1; determined by NMR analysis) by following the procedure for the synthesis of 7.

IR $v_{max}$ (film): 3076, 3022, 1733, 1647 cm$^{-1}$; $^1$H NMR (500 MHz, CDCl$_3$): (major) δ 6.51 (1H, m), 6.10 (1H, m), 5.87 (1H, m), 5.57 (1H, app t, J=3.7 Hz), 5.30 (1H, dd, J=17.3, 1.2 Hz), 5.22 (1H, app d, J=10.2 Hz), 4.58 (2H, br d, J=5.7 Hz), 3.19 (1H, br d, J=3.3 Hz), 2.99 (1H, m), 2.79 (1H, m), 0.50 (2H, m), 0.43 (2H, m); $^{13}$C NMR (125 MHz, CDCl$_3$): (major) δ 170.5, 139.1, 133.2, 131.5, 118.8, 87.2, 65.8, 52.6, 51.1, 50.6, 43.3, 8.1, 4.5; HRMS calculated for $C_{13}H_{15}NNaO_4^+$ [M+Na]$^+$: 272.0899, found 272.0890.

The above obtained nitro adduct (1.3 g) was reduced to corresponding amine 9a and 9b (1.1 g) as a brown liquid in 80% yield by following the procedure for the synthesis of 7.

IR $v_{max}$ (film): 3684, 3584, 3020, 1722, 1524 cm$^{-1}$; $^1$H NMR (500 MHz, CDCl$_3$): (major) δ 6.47 (1H, m), 6.27 (1H, dd, 5.7, 2.7 Hz), 5.89 (1H, m), 5.29 (1H, dd, J=17.0, 1.5 Hz), 5.21 (1H, app d, J=10.0 Hz), 4.58 (2H, d, J=5.5 Hz), 3.94 (1H, m), 2.57 (1H, m), 2.26 (1H, m), 1.97 (1H, d, J=3.9 Hz), 1.81 (2H, br s), 0.47 (1H, m), 0.39 (2H, m), 0.32 (1H, m); $^{13}$C NMR (125 MHz, CDCl$_3$): (major) δ 173.3, 138.6, 133.8, 132.2, 118.2, 65.1, 57.0, 55.5, 54.0, 51.0, 43.8, 8.2, 4.3; LCMS

Example 8

(R,E)-allyl 3-(2,4-dihydroxy-3,3-dimethylbutana-mido)acrylate (10) (FIG. 6)

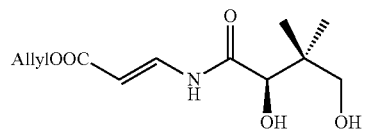

Prepared by following the procedure[7] for the synthesis of 4 (one-pot procedure) by using 9 a/b (100 mg, 0.4 mmol) and D-(−)-pantolactone (118 mg, 0.8 mmol) in a 52% yield (55 mg).

IR $\nu_{max}$ (film): 3344, 2964, 2931, 2877, 1687, 1633 cm$^{-1}$; $^1$H NMR (400 MHz, CD$_3$OD, 3.31): δ 7.98 (1H, d; J=14.3 Hz), 5.98 (1H, ddt, J=17.3, 10.5, 5.5 Hz), 5.78 (1H, d, J=14.3 Hz), 5.34 (1H, dd, J=17.3, 1.5 Hz), 5.24 (1H, dd, J=10.5, 1.2 Hz), 4.65 (2H, app dt, J=6.7, 5.5 Hz), 4.05 (1H, s), 3.50 (1H, d, J=10.8 Hz), 3.39 (1H, d, J=10.8 Hz), 0.96 (3H, s), 0.95 (3H, s); $^{13}$C NMR (50 MHz, CDCl$_3$): δ 171.3, 167.1, 136.8, 132.2, 118.1, 102.3, 77.9, 71.51, 64.9, 39.3, 20.9, 20.1; LCMS [M+Na]$^+$: 280. [α]$_D^{24}$=+73.2° (c=0.75, CH$_3$CN); Lit.$^{5c}$ [α]$_D^{25}$=+80.0° (c=0.12, CH$_3$CN). All the spectral data compared with that of reported data and found to be identical.

Advantages of the Invention

Present invention provides an efficient and rapid synthesis of anti plasmodial and anti bacterial agent CJ-15801 and cis CJ-15801 by reducing the number of steps, following atom economy, and a green synthetic route.

The invention claimed is:

1. A process for the preparation of compound of general formula I:

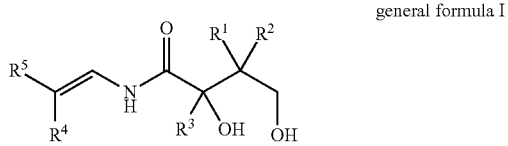

general formula I wherein R$^1$—, R$^2$, and R$^3$ are independently selected from the group consisting of hydrogen; —C$_1$-C$_{15}$ alkyl; —C$_1$-C$_{15}$ alkenyl; —C$_1$-C$_{15}$ alkynyl; phenyl; aralkyl; and a conjugated aromatic group; each of which is optionally substituted with halo; nitro; alkoxy; cyano; hydroxy; amido; or amino groups; or R$^1$ and R$^2$ taken together form a cyclic compound which optionally contains 1 to 4 heteroatoms and optionally contains a carbonyl group; or R$^1$ and R$^2$ are independently selected from the group consisting of halo group; nitro group; alkoxy group; cyano group; hydroxyl group; amido groups; and amino groups;

R$^4$ and R$^5$ are independently selected from the group consisting of hydrogen; —C$_1$-C$_{15}$ alkyl; —C$_1$-C$_{15}$ alkenyl, —C$_1$-C$_{15}$ alkynyl; phenyl; aralkyl; conjugated aromatic group; which is optionally substituted with halo; nitro; alkoxy; cyano; hydroxy; amido or amino groups; or R$^4$ and R$^5$ independently are COOR; or R$^4$ and R$^5$ taken together form a cyclic compound which optionally contains 1 to 4 heteroatoms and optionally contains a carbonyl group; and R is independently selected from the group consisting of hydrogen, —C$_1$-C$_{15}$ alkyl, —C$_1$-C$_{15}$ alkenyl; —C$_1$C$_{15}$ alkynyl; phenyl; and aralkyl; each of which is optionally substituted with a substituent selected from the group consisting of halo; nitro; alkoxy; cyano; hydroxy; amido groups and amino groups; and the process comprising the steps of:

(i). heating a mixture of amine (A) and D-(−)-pantolactone (B) in the ratio ranging from 1:1.5 to 1:2 in a solvent at a temperature in the range of 110 to 150° C. for a period in the range of 16 to 24 hours followed by raising the temperature of the mixture to a temperature in the range of 200-230° C. for a period in the range of 15 to 25 minutes to obtain a crude reaction mixture;

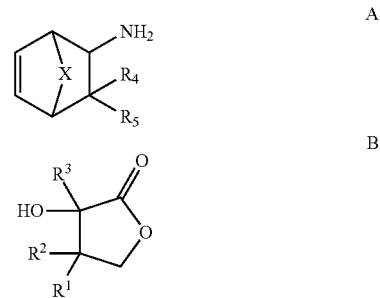

wherein R$^1$, R$^2$, R$^3$, R$^4$ and R$^5$ in formulas (A) and (B) are defined above; and (ii). cooling the crude reaction mixture as obtained in step (i) at a temperature in the range of 25 to 30° C. followed by purifying by silica gel column chromatography to obtain the compound of general formula I.

2. The process of claim 1, wherein the solvent used in step (i) is selected from the group consisting of cyclohexane, benzene, toluene, xylene, diphenylether; anisole and dioxane.

3. The process of claim 1, wherein the compound of general formula I is:

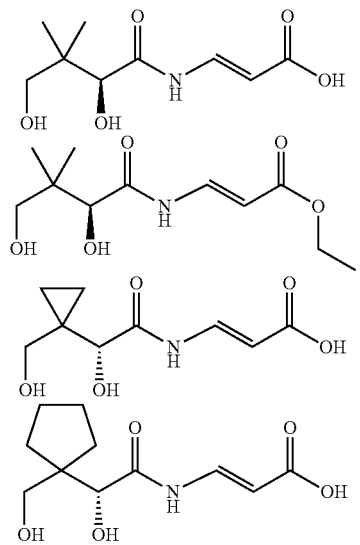

-continued

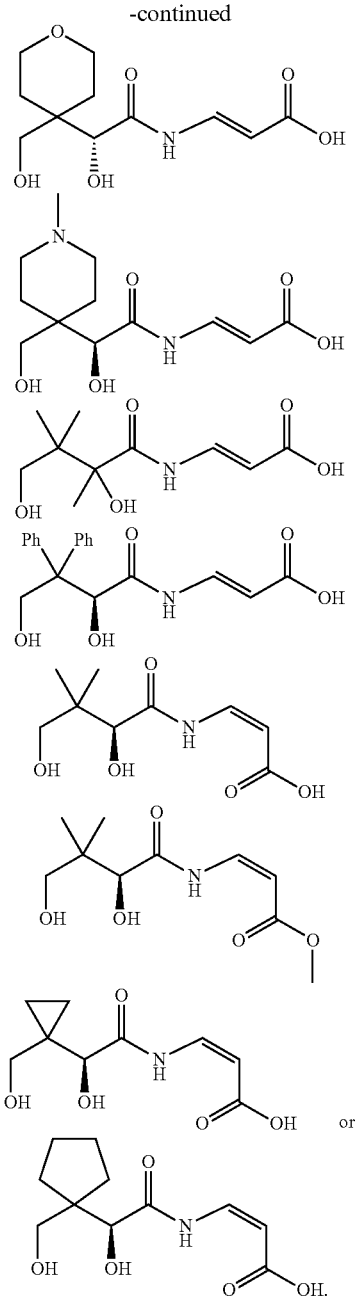

4. A process for the preparation of compound cis CJ-15,801, said process comprising the steps of:
  (i). heating a mixture of

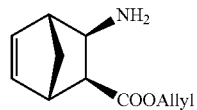

and D-(−)-pantolactone in the ratio ranging from 1:1.5 to 1:2 in a solvent at a temperature in the range of 110 to 150° C. for a period in the range of 16 to 24 hours followed by raising the temperature of the mixture to a temperature in the range of 15 to 25 minutes to obtain a crude reaction mixture;

(ii). cooling the crude reaction mixture as obtained in step (i) at a temperature in the range of 25 to 30° C. followed by purifying by silica gel column chromatography to yield a cis isomer

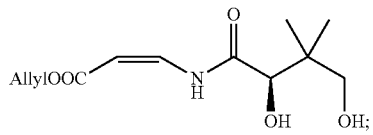

(iii). deallylating the cis isomer as obtained in step (ii) in the presence of a catalyst in a solvent to obtain cis CJ-15,801.

5. The process of claim 4, wherein the catalyst used in step (iii) is selected from the group consisting of $PdCl_2$, $PdCl(PPh_3)_4$, and $Pd(PPh_3)_4$.

6. The process of claim 1, wherein $R^4$ is H and $R^5$ is COOR, in which R is allyl.

7. The process of claim 6, further comprising deallylating the compound obtained in step (ii) to form a compound of the following formula or a stereoisomer thereof:

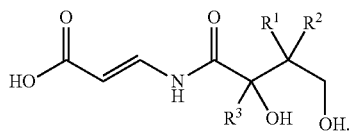

* * * * *